United States Patent [19]
Yashima et al.

[11] Patent Number: 5,312,915
[45] Date of Patent: May 17, 1994

[54] PROCESS FOR PRODUCING EPSILON-CAPROLACTAM

[75] Inventors: Tatsuaki Yashima; Takayuki Komatsu, both of Tokyo, Japan

[73] Assignee: Sumitomo Chemical Company, Limited, Osaka, Japan

[21] Appl. No.: 118,721

[22] Filed: Sep. 10, 1993

[30] Foreign Application Priority Data

Mar. 4, 1993 [JP] Japan ................................ 5-043845

[51] Int. Cl.$^5$ ............................................ E07D 201/04
[52] U.S. Cl. .................................................... 540/536
[58] Field of Search ......................................... 540/536

[56] References Cited

U.S. PATENT DOCUMENTS

| | | | |
|---|---|---|---|
| 3,503,958 | 3/1970 | Landis | 540/536 |
| 4,359,421 | 11/1982 | Bell et al. | 540/536 |
| 4,709,024 | 11/1987 | Sato et al. | 540/536 |
| 4,927,924 | 5/1990 | Bell et al. | 540/536 |

OTHER PUBLICATIONS

Lectures for publishing Research on Chemical Utilization of Carbon Resources, 1992 with our English translation, The Society of Polymer Science, Japan.

64th Autumn Annual Meeting of the Chemical Society of Japan, Preliminary Contributions for the Lectures I, Symposium, Chemical Society of Japan, Union Conference of Chemistry-relating Societies and Associations. Manuscripts for slide viewers use by K. Miura et al at "Lectures for publishing Research on the Chemical Utilization of Carbon Resources", with our English translation, 1992.

Manuscripts for slide viewers use by Mr. K. Miura et al at 64th Autumn Annual Meeting of the Chemical Society of Japan with our English translation.

*Primary Examiner*—Robert T. Bond
*Attorney, Agent, or Firm*—Cushman, Darby & Cushman

[57] ABSTRACT

$\epsilon$-Caprolactam is produced efficiently with high selectivity by contacting cyclohexanone oxime in gas phase with a solid catalyst which is a crystalline zeolite having a pore size smaller than molecular size of cyclohexanone oxime or a crystalline zeolite having closed pores.

11 Claims, 3 Drawing Sheets

INFLUENCE OF W/F IN BECKMANN REARRANGEMENT
OF CYCLOHEXANONE OXIME
CATALYST: HZSM-5
REACTION TEMPERATURE: 320°C

INFLUENCE OF REACTION TEMPERATURE IN BECKMANN
REARRANGEMENT OF CYCLOHEXANONE OXIME
CATALYST: HZSM-5
W/F: 10.2 g·h·mol$^{-1}$

ADSORPTION CURVE OF CYCLOHEXANONE OXIME
ADSORPTION TEMPERATURE: 120 °C

ADSORPTION CURVE TO ZSM-5
ADSORPTION TEMPERATURE: 120 °C

LOW TEMPERATURE
(REACTION TAKES PLACE MAINLY ON THE OUTER SURFACE)

ZSM-5

HIGH TEMPERATURE
(REACTION TAKES PLACE ALSO IN PORES)

ZSM-5

Process for Producing Epsilon-Caprolactam

PROCESS FOR PRODUCING EPSILON-CAPROLACTAM

BACKGROUND OF THE INVENTION

The present invention relates to a process for producing ε-caprolactam and more particularly, to a process for producing ε-caprolactam from cyclohexanone oxime, characterized by using a crystalline zeolite having a specific pore size or a crystalline zeolite having closed pores.

ε-Caprolactam is an important raw material for nylon and the like and has, hitherto, been produced by liquid phase Beckmann rearrangement of cyclohexanone oxime using fuming sulfuric acid or concentrated sulfuric acid as a catalyst.

However, this process suffers from the problems such as need of fuming sulfuric acid in a large amount and by-production of ammonium sulfate in a large amount.

For solving these problems, it has been proposed to carry out gas-phase rearrangement using solid catalysts such as crystalline zeolites, for example, ZSM-5 (Japanese Patent Application Kokai Nos. 57-139062 and 62-123167). In this case, however, the selectivity for ε-caprolactam formation and the like are not enough and further improvement in this respect has been demanded.

Under the circumstances, in order to find a further improved process for producing ε-caprolactam, the inventors have conducted intensive research on crystalline zeolites as catalysts. As a result, it has been found that cyclohexanone oxime adsorbed into the pores of the zeolites brings about side reaction to cause reduction in the selectivity and it has been further found that the selectivity for ε-caprolactam formation is remarkably improved by using crystalline zeolites having a specific pore size or crystalline zeolites having closed pores.

SUMMARY OF THE INVENTION

That is, the present invention provides a superior process for producing ε-caprolactam by contacting cyclohexanone oxime in gas phase with a solid catalyst, characterized in that a crystalline zeolite having a pore size smaller than the molecular size of cyclohexanone oxime or a crystalline zeolite having closed pores is used as the solid catalyst.

DESCRIPTION OF THE INVENTION

Figure 1:
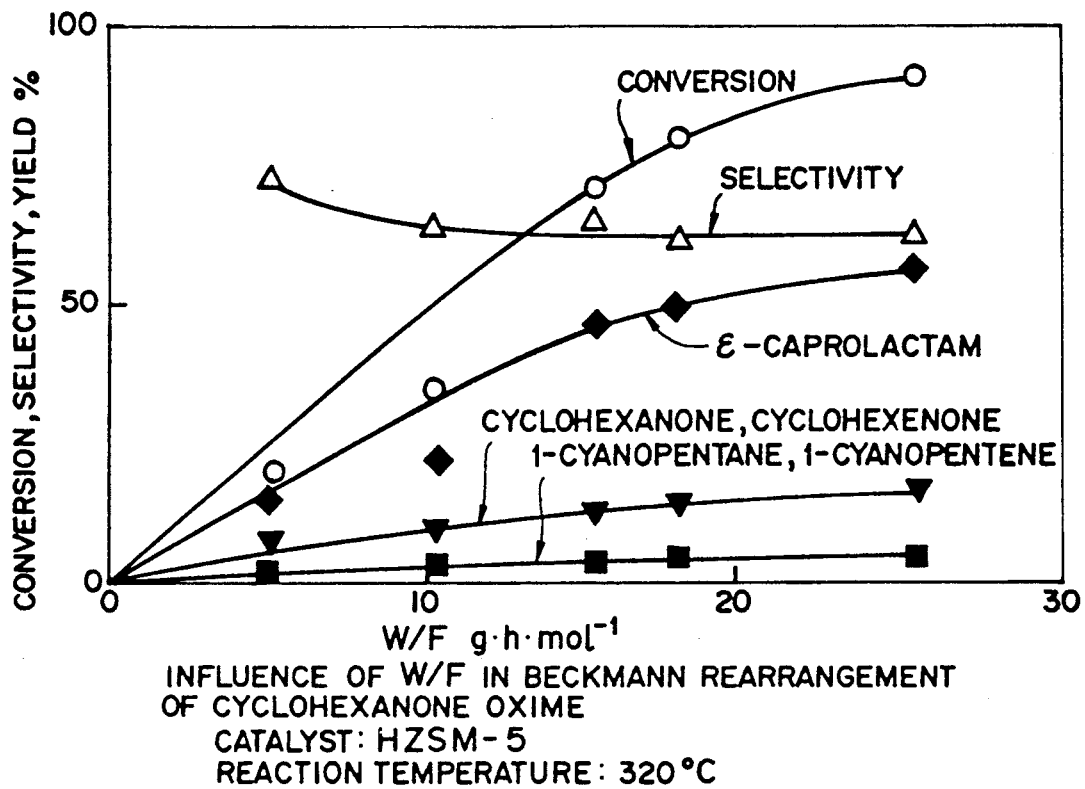
FIG. 1 is a graph which shows the relations between W/F and conversion, selectivity and yield on HZSM-5.

The present invention is explained in detail.

The present invention is characterized by using as a solid catalyst a crystalline zeolite having a pore size smaller than molecular size of cyclohexanone oxime or a crystalline zeolite having closed pores. When a crystalline zeolite having a pore size not smaller than the molecular size of cyclohexanone oxime is used, ring-opened compounds such as 1-cyanopentane and 1-cyanopentene are produced in large amounts as by-products in addition to cyclic ketones such as cyclohexanone and cyclohexenone and the selectivity for the desired ε-caprolactam formation lowers. Therefore, the specific crystalline zeolites as mentioned above which selectively bring about the reaction outside the pores are used in the present invention.

The crystalline zeolites having a pore size smaller than molecular size of cyclohexanone oxime include, for example, ferrierite, A-type zeolite, chabazite, erionite, zeolite ρ, EU-1 and zeolite θ1. Among them, ferrierite and A-type zeolite are preferred. Furthermore, the crystalline zeolites having closed pores include, for example, proton-type crystalline zeolites filled with template and crystalline zeolites having pores in which an oxide of magnesium, phosphorus, boron or the like is produced by impregnating the zeolites with a compound of magnesium, phosphorus, boron or the like. The proton-type crystalline zeolites filled with template are preferred.

The crystalline zeolites used in the present invention may be converted into $H^+$ form by subjecting them to ion-exchange with aqueous ammonium chloride, dilute hydrochloric acid or the like or they may be converted into polyvalent metal ion exchanged-form by subjecting them to ion-exchange with an aqueous solution containing alkaline earth metal ions or lanthanoid metal ions such as $Ca^{2+}$, $Mg^{2+}$, $Sr^{2+}$, $Ba^{2+}$, $La^{3+}$ and $Ce^{3+}$.

Gas phase catalytic method in a fixed bed or fluidized bed is generally used for reaction of cyclohexanone oxime. When a fixed bed is used, the starting material cyclohexanone oxime is vaporized and then is brought into contact with the catalyst bed. When a fluidized bed is used, cyclohexanone oxime may be directly introduced into the catalyst bed without vaporization.

Furthermore, the reaction can also be carried out in the presence of a gas which is inert to the reaction. Examples of such gas are helium, nitrogen, carbon dioxide, benzene, toluene and cyclohexane.

Reaction temperature is usually 250°–500° C., preferably 300°–450° C.

The space velocity of the starting material cyclohexanone oxime is usually WHSV=0.1–40 $hr^{-1}$ (feeding speed of cyclohexanone oxime per 1 kg of the catalyst: 0.1–40 kg/hr), preferably 0.2–20 $hr^{-1}$, more preferably 0.5–10 $hr^{-1}$.

Isolation of ε-caprolactam from the reaction mixture can be effected by usual methods. For example, a reaction mixture gas is cooled and condensed and then evaporated, extracted or crystallized to obtain a purified ε-caprolactam.

Thus, ε-caprolactam is produced. According to the present invention, the selectivity for ε-caprolactam formation can be improved and ε-caprolactam can be effectively produced by using a specific zeolite, namely, a crystalline zeolite having a pore size smaller than molecular size of cyclohexanone oxime or a crystalline zeolite having closed pores.

The present invention is explained by the following nonlimiting examples.

The beckmann rearrangement reaction was effected by packing 0.87 g of powdered zeolite in a quartz glass tube of 72 cm in length and 1.7 cm in inner diameter, heat treating the zeolite in a He stream at 450° C. for 1 hour, thereafter cooling the zeolite to a given temperature and then feeding a 15 wt% cyclohexanone oxime/benzene solution to the tube.

He was used as a carrier gas. Partial pressures were 4.15 kPa for cyclohexanone oxime, 35.8 kPa for benzene and 61.2 kPa for He. The reaction conditions were 320° C. and contacting time W/F (catalyst weight g/(benzene+oxime+helium) mol/h)=10.2 g·h/mol unless otherwise stated. Analysis was conducted by internal standard method using gas chromatograph.

The crystalline zeolites used were prepared in the following manner.

① H-ZSM-5 (Si/Al=20, pore size=5.6×5.3 Å)

A solution comprising 315 g of deionized water, 47.3 g of $Al_2(SO_4)_3 \cdot 14-18H_2O$, 39.5 g of tetrapropylammonium bromide and 15.0 g of sulfuric acid and a solution comprising 233 g of deionized water and 363 g of sodium silicate ($SiO_2$: 28.7%, $Na_2O$: 9.42%) were added together to a solution comprising 548 g of deionized water and 140 g of NaCl over a period of 2 hours so that pH of the mixture reached 9-11. At the end of addition, the pH of the mixture was 9.8.

Then, the mixture was charged in a Teflon liner and hydrothermal synthesis was effected in an autoclave. That is, the content was heated to 165° C. over a period of 2 hours at a stirring rate of 130 rpm and reaction was carried out at that temperature for 40 hours. The product was washed, filtrated and then dried at 110° C. for 16 hours and furthermore calcined in the air at 530° C. to remove the organic template to obtain white powders. X-ray diffraction pattern of the powders coincided with that of powders having MFI structure.

The resulting ZSM-5 type zeolite was subjected to ion exchange using a 0.1 mol/l $NH_4NO_3$ solution for 3 days and the obtained $NH_4$-ZSM-5 was washed, filtrated and dried at 110° C. and calcined in the air at 500° C. for 5 hours to obtain H-ZSM-5.

② H-SAPO-5 (Si/P=0.12, Al/P=0.92, pore size=7.3×7.3 Å, obtained by replacing a part of an aluminosilicate with silicon)

A 85% aqueous $H_3PO_4$ solution was added to a solution comprising 86.6 ml of deionized water and 51.1 g of $Al(OC_3H_7)_3$ (at least 95% in purity), followed by stirring for 1 hour. This was charged in a Hastelloy liner and transferred to an autoclave and thereto was added a solution comprising 8 ml of Cataloid S-20L (manufactured by Shokubai Kasei Co.) and 128.3 ml of a 20-25% aqueous tetrapropylammonium hydroxide solution, followed by stirring for 2 hours. Then, hydrothermal synthesis was carried out by stirring at 195° C. for 48 hours. The product was washed and centrifuged and dried at 110° C. for 16 hours and furthermore calcined in the air at 550° C. for 48 hours to remove the organic matter to obtain white powders.

X-ray diffraction pattern of the powders coincided with that of powders having AFI structure. Inductively coupled plasma spectrometry (ICP analysis) revealed that Si was contained and $NH_3$-TPD measurement revealed that acid point was present. Thus, it was confirmed that Si was introduced into the crystal skeleton.

Then, in the same manner as in the above ①, the resulting white powders were subjected to ion exchange, drying and calcination to obtain H-SAPO-5.

③ H-borosilicate [ZSM-5 type, Si/B=50 (charging ratio), template in the pores was not removed]

A solution comprising 50 g of deionized water and 13.5 g of sodium carbonate was added dropwise to a solution comprising 650 g of deionized water and 60 g of Cab-osil (manufactured by Flka Chemika) with adjusting pH to 9-10 with 1 mol/l $H_2SO_4$. With adjusting pH to 9.2 with the above $H_2SO_4$, thereto was added dropwise a solution comprising 100 g of deionized water, 1.2 g of $H_3BO_3$ and 67.1 g of tetraamonium bromide (manufactured by Tokyo Kasei Co.).

Then, this was charged in a Teflon liner and the liner was transferred in an autoclave and hydrothermal synthesis was effected at 150° C. for 72 hours at 130 rpm. The product was filtrated, washed and then dried at 110° C. and furthermore, calcined for 12 hours at 330° C. (confirming that the releasing temperature of template was 340° C. or higher) to obtain powders.

Then, the resulting powders were subjected to ion exchanging and drying in the same manner as in the above ① and further calcined at 300° C. for 12 hours to obtain an H-borosilicate.

④ H-mordenite (Si/Al=58, pore size=7.0×6.5 Å, obtained by subjecting a mordenite of Si/Al=5 to heat treatment and acid treatment to remove aluminum)

H-mordenite manufactured by Nippon Chemical Co. was calcined in the air at 700° C. for 12 hours and then refluxed in an aqueous nitric acid solution of 6 mol/l for 10 hours to obtain H-mordenite from which aluminum was removed.

⑤ H-ferrierite (Si/Al=10, pore size=5.4×4.2 Å)

Ferrierite manufactured by Tosoh Co. was subjected to ion exchanging, drying and calcination in the same manner as in the above ① to obtain H-ferrierite.

⑥ Ca-A (Si/Al=1, pore size=5×5 Å)

Molecular sieves 5A manufactured by Nishio Kogyo Co. were washed with deionized water to obtain the desired product.

REFERENTIAL EXAMPLE 1

Reaction was carried out using H-ZSM-5 with changing W/F from 5 to 25 g·h/mol. The reaction temperature was 320° C. and sampling was carried out for the period of 30-60 minutes after starting of the reaction and the samples were analyzed. The results are shown in FIG. 1.

With increase in W/F, the conversion increased from 20% to 91%, but the selectivity was kept at about 65%. Furthermore, yield of the desired ε-caprolactam and yields of cyclic ketones such as cyclohexanone and cyclohexenone and ring-opened products such as 1-cyanopentane and 1-cyanopentene which were by-products monotonously increased like the conversion.

From these results, it can be seen that the by-products are not produced by consecutive reactions with ε-caprolactam which is a main product, but are mainly produced by a reaction which takes place concurrently with the main reaction.

REFERENTIAL EXAMPLE 2

Figure 2:
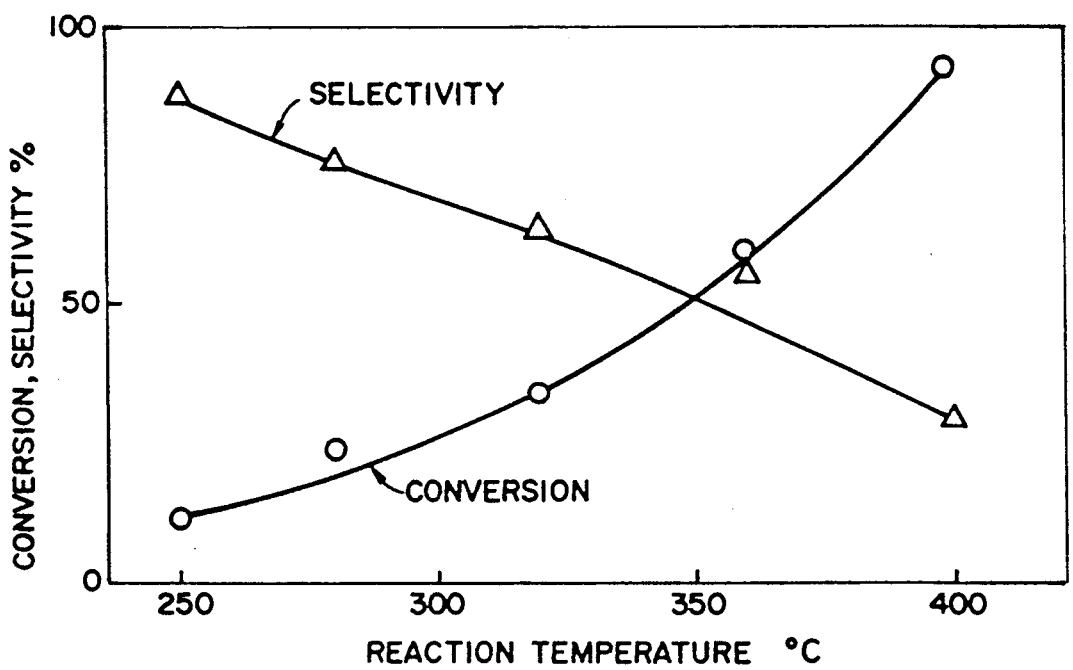
FIG. 2 is a graph which shows the relations between reaction temperature and conversion and selectivity on HZSM-5.

Reaction was carried out using H-ZSM-5 with changing the reaction temperature from 250° C. to 400° C. W/F was 10.2 g·h/mol and sampling was carried out for a period of 30-60 minutes after starting of the reaction and the samples were analyzed. The results are shown in FIG. 2.

With increase in the reaction temperature, the conversion increased from 11% to 93%, but the selectivity decreased from 88% to 30%. It can be seen therefrom that the percentage of the side-reactions taking place increases at high temperatures.

REFERENTIAL EXAMPLE 3

In order to elucidate the relation between the pore size of ZSM-5 and the size of molecules such as cyclohexanone oxime and ε-caprolactam, measurement of adsorption at 120° C. was conducted using a quartz spring scale.

(1) Cyclohexanone oxime

Figure 3:
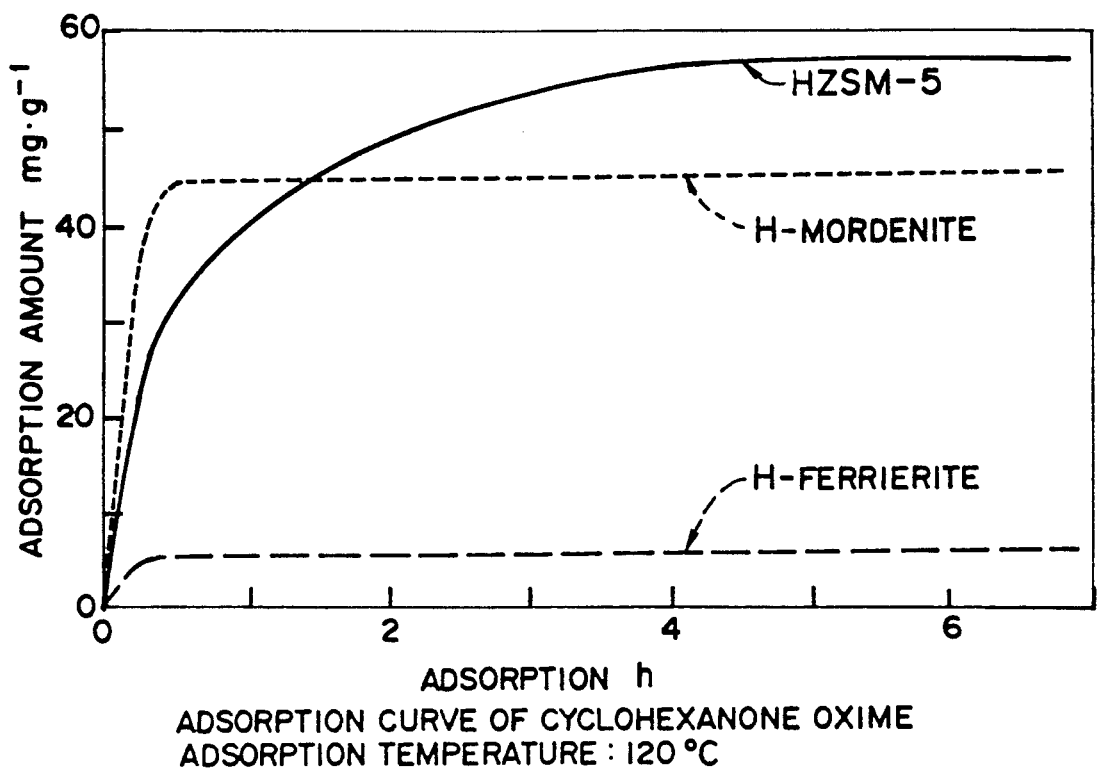
FIG. 3 is a graph which shows the relation between adsorption amount and adsorption time of cyclohexanone oxime in various zeolites.

The results of measurement on ZSM-5 are shown in FIG. 3 together with the results of measurement on mordenite larger than ZSM-5 in pore size and ferrierite smaller than ZSM-5 in pore size. Equilibrium adsorption amounts after 5 hours are 56.4, 44.6 and 5.7 mg/g, respectively and by comparing with pore volume calculated from the respective crystal structures it can be seen that cyclohexanone oxime enters into the pores and is adsorbed therein in the case of mordenite and ZSM-5.

On the other hand, it can be seen that in the case of ferrierite, cyclohexanone oxime is not able to enter into the pores and is adsorbed to only the external surface of crystal in view of the fact that the adsorption amount is considerably smaller than pore volume.

Furthermore, when a comparison is made between mordenite and ZSM-5 where cyclohexanone oxime is adsorbed into the pores, much longer time is required for reaching equilibrium adsorption in ZSM-5 than in mordenite. Thus, it can be seen that diffusion of cyclohexanone oxime in the pores of ZSM-5 is very slow and therefore, molecular size of cyclohexanone oxime is nearly the same as the pore size of ZSM-5.

(2) ε-caprolactam

Figure 4:
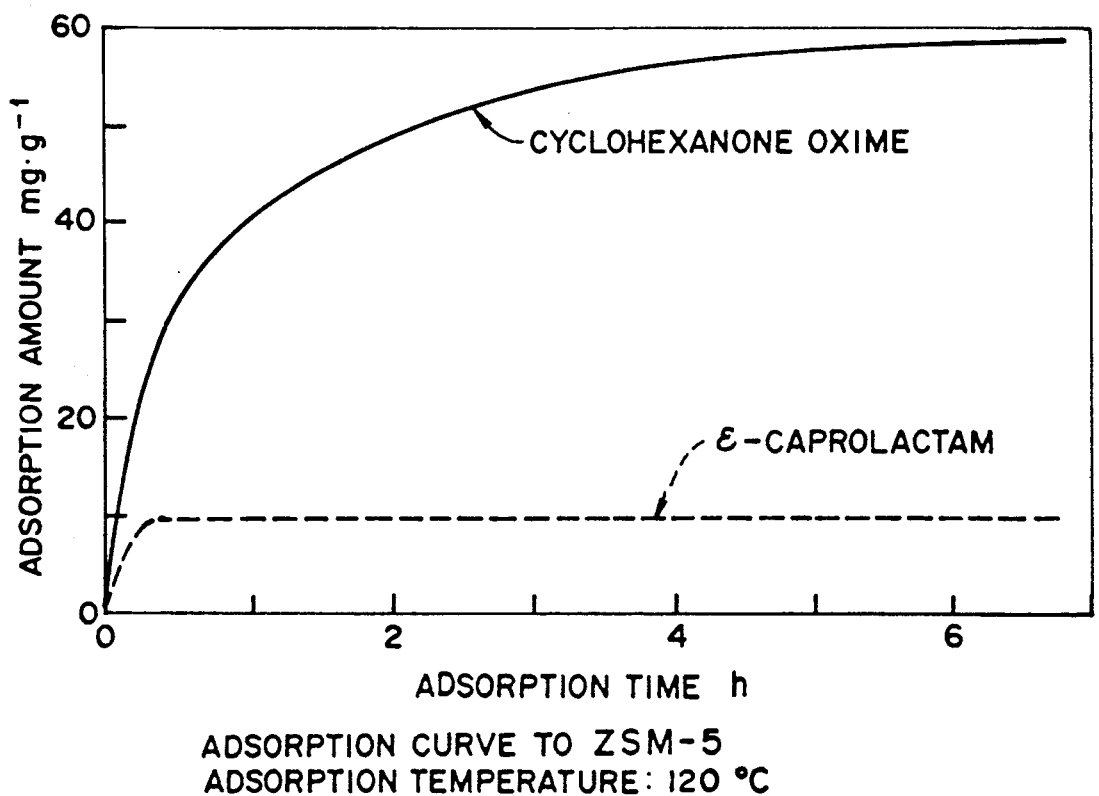
FIG. 4 is a graph which shows the relation between adsorption amount and adsorption time ε-caprolactam and cyclohexanone oxime in ZSM-5.

Results of measurement on ZSM-5 are shown in FIG. 4 together with the results in the above (1). ε-Caprolactam reached adsorption equilibrium in a short time and the equilibrium adsorption amount was much smaller than cyclohexanone oxime.

From these results, it can be seen that ε-caprolactam cannot be adsorbed into the pores of ZSM-5 at 120° C. and is adsorbed only to the external surface of the crystal, namely, ε-caprolactam is not produced in the pores of ZSM-5 or even if produced, it hardly diffuses to the outside of the pores.

Figure 5:
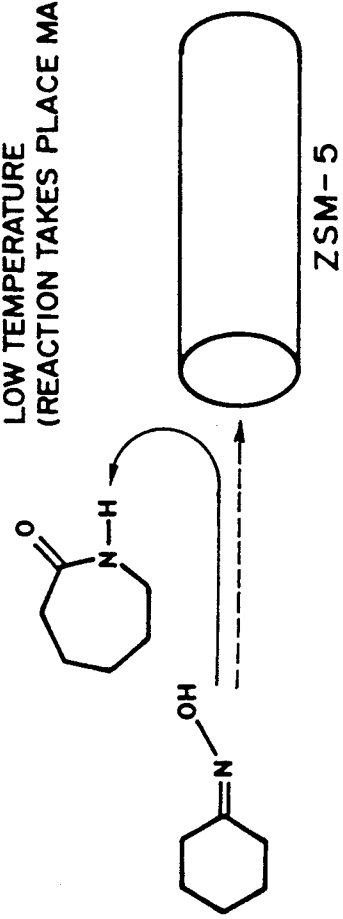
FIG. 5 is a suppositive diagram of reaction of cyclohexanone oxime in ZSM-5.
Figure 5:
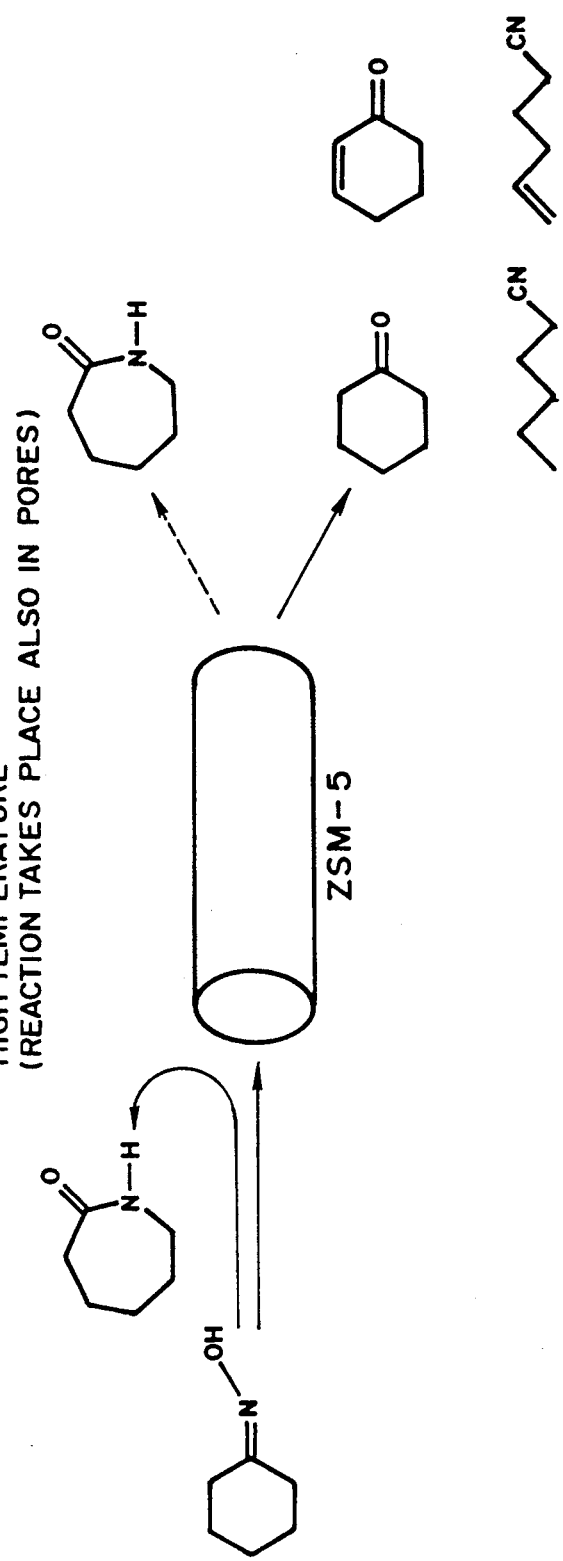

It is considered from these results that side-reactions proceed preferentially to the rearrangement reaction of cyclohexanone oxime which has entered the pores of ZSM-5 to ε-caprolactam. That the selectivity decreased with increase in reaction temperature in Referential Example 2 is considered to be because more cyclohexanone oxime which is the reactant enters the pores with increase in temperature and side-reactions proceed in the pores. (FIG. 5).

EXAMPLE 1

Rearrangement reaction was carried out using Ca-A (Si/Al=1, pore size=5×5 Å) as a catalyst. Sampling was conducted three times, namely, for 30-60 minutes, 60-90 minutes and 90-120 minutes after starting of flowing. Average selectivity of the three analytical values (hereinafter referred to as "average selectivity for 30-120 minutes") is shown in Table 1.

EXAMPLE 2

Rearrangement reaction was carried out using H-ferrierite (Si/Al=10, pore size=5.4×4.2 Å manufactured by Toso Co.) as a catalyst. The average selectivity for 30-120 minutes after starting of flowing is shown in Table 1.

EXAMPLE 3

Rearrangement reaction was carried out using H-borosilicate (ZSM-5 type, a catalyst having pores from which template was not removed) as a catalyst. The average selectivity for 30-120 minutes after starting of flowing is shown in Table 1.

COMPARATIVE EXAMPLE 1

Rearrangement reaction was carried out using H-ZSM-5 (Si/Al=20, pore size=5.6×5.3 Å) as a catalyst. The average selectivity for 30-120 minutes after starting of flowing is shown in Table 1.

COMPARATIVE EXAMPLE 2

Rearrangement reaction was carried out using H-mordenite (Si/Al=58, pore size=7.0×6.5 Å obtained by subjecting H-mordenite having Si/Al=5 to heat treatment and acid treatment to remove aluminum) as a catalyst. The average selectivity for 30-120 minutes after starting of flowing is shown in Table 1.

COMPARATIVE EXAMPLE 3

Rearrangement reaction was carried out using H-SAPO-5 (Si/P=0.12, Al/P=0.92, pore size=7.3×7.3 Å obtained by replacing a part of aluminophosphate with silicon) as a catalyst. The average selectivity for 30-120 minutes after starting of flowing is shown in Table 1.

TABLE 1

| Example | Catalyst | Pore size (Å) | Selectivity (%) |
|---|---|---|---|
| Example 1 | Ca-A | 5 × 5 | 94.3 |
| Example 2 | H-ferrierite | 5.4 × 4.2 | 92.0 |
| Example 3 | H-borosilicate | — | 93.9 |
| Comparative Example 1 | H-ZSM-5 | 5.6 × 5.3 | 62.4 |
| Comparative Example 2 | H-mordenite | 7.0 × 6.5 | 71.3 |
| Comparative Example 3 | H-SAPO-5 | 7.3 × 7.3 | 76.7 |

What is claimed is:

1. A process for producing ε-caprolactam by contacting cyclohexanone oxime in gas phase with a solid catalyst, wherein a crystalline zeolite having a pore size smaller than molecular size of cyclohexanone oxime or a crystalline zeolite having closed pores is used as the solid catalyst.

2. A process according to claim 1, wherein the solid catalyst is a crystalline zeolite having a pore size smaller than molecular size of cyclohexanone oxime.

3. A process according to claim 2, wherein the crystalline zeolite is ferrierite.

4. A process according to claim 2, wherein the crystalline zeolite is A type zeolite.

5. A process according to claim 1, wherein the solid catalyst is a crystalline zeolite having closed pores.

6. A process according to claim 1, wherein the crystalline zeolite having the closed pores is a proton type crystalline zeolite having pores filled up with template.

7. A process according to claim 6, wherein the crystalline zeolite is a borosilicate.

8. A process according to claim 1 which is carried out by a gas phase catalytic method using a fixed bed or a fluidized bed.

9. A process according to claim 1 which is carried out in the presence of a gas inert to the reaction.

10. A process according to claim 1 which is carried out at 250°–500° C.

11. A process according to claim 1, wherein the space velocity WHSV of the starting cyclohexanone oxime is 0.1–40 hr$^{-1}$.

* * * * *